(12) United States Patent
Oberdoerfer et al.

(10) Patent No.: US 8,739,630 B2
(45) Date of Patent: Jun. 3, 2014

(54) PULSE-ECHO METHOD FOR DETERMINING THE DAMPING BLOCK GEOMETRY

(75) Inventors: York Oberdoerfer, Langenfeld (DE); Michael Berke, Cologne (DE); Wolf-Dietrich Kleinert, Bonn (DE); Jerome Poirier, Saulx les Chatreux (FR); Sascha Schieke, Greer, SC (US)

(73) Assignee: GE Sensing & Inspection Technology (DE)

( * ) Notice: Subject to any disclaimer, the term of this patent is extended or adjusted under 35 U.S.C. 154(b) by 608 days.

(21) Appl. No.: 13/062,221

(22) PCT Filed: Sep. 7, 2009

(86) PCT No.: PCT/EP2009/061579
§ 371 (c)(1),
(2), (4) Date: Jun. 22, 2011

(87) PCT Pub. No.: WO2010/026252
PCT Pub. Date: Mar. 11, 2010

(65) Prior Publication Data
US 2011/0239768 A1    Oct. 6, 2011

(30) Foreign Application Priority Data

Sep. 5, 2008 (DE) .......................... 10 2008 041 831

(51) Int. Cl.
*G01N 29/07* (2006.01)
*G01N 29/32* (2006.01)

(52) U.S. Cl.
USPC ................................ 73/627; 73/597; 73/622

(58) Field of Classification Search
USPC ............ 73/627, 597, 598, 602, 622, 626, 628
See application file for complete search history.

(56) References Cited

U.S. PATENT DOCUMENTS 3,844,163 A * 10/1974 Di Leo ............................ 73/597
4,354,388 A * 10/1982 Diepers et al. .................. 73/612
(Continued)

FOREIGN PATENT DOCUMENTS

DE    3327526 C2    4/1984
DE    3441894 A1    7/1986
(Continued)

OTHER PUBLICATIONS

Song S-J et al: "Simulation of 3-D radiation beam patterns propagated through a planar interface from ultrasonic phased array transducers"; Ultrasonics, IPC Science and Technology, vol. 40, No. 1-8, May 1, 2002, pp. 519-524; XP004357251.

(Continued)

*Primary Examiner* — J M Saint Surin
(74) *Attorney, Agent, or Firm* — Cantor Colburn LLP

(57) ABSTRACT

The invention relates to a nondestructive ultrasonic test method in which at least one ultrasonic pulse is emitted into a workpiece under test by means of at least one ultrasonic transmitter (3), the ultrasonic pulse is reflected on boundary surfaces within the workpiece, the reflected ultrasound is received by at least one ultrasonic receiver (2), and the associated signals are evaluated, the ultrasound penetrating a damping block (4) that is arranged between the workpiece and the transmitter or receiver. Said method is characterized in that it includes at least one step for determining at least one dimension (alpha, $d_1$, $d_2$) of the damping block (4) that is relevant for the ultrasonic test; in said step, the propagation time of at least one ultrasonic pulse which is generated by the ultrasonic transmitter (3), is reflected on a boundary surface (5) of the damping block (4), and is received by the ultrasonic receiver (2) is measured, and at least one dimension (alpha, $d_1$, $d_2$) of the damping block (4) that is relevant for the ultrasonic test is determined from said measurement.

7 Claims, 1 Drawing Sheet

(56) References Cited

U.S. PATENT DOCUMENTS

| | | | | |
|---|---|---|---|---|
| 4,413,517 A * | 11/1983 | Soden | | 73/597 |
| 4,658,649 A * | 4/1987 | Brook | | 73/624 |
| 5,115,681 A * | 5/1992 | Bouheraoua et al. | | 73/801 |
| 5,565,628 A * | 10/1996 | Lorraine | | 73/642 |
| 7,194,907 B2 * | 3/2007 | Abbate et al. | | 73/597 |
| 7,516,664 B2 * | 4/2009 | Meier et al. | | 73/644 |
| 7,757,558 B2 * | 7/2010 | Bossi et al. | | 73/609 |
| 8,402,830 B2 * | 3/2013 | Kleinert et al. | | 73/629 |
| 2009/0320601 A1 * | 12/2009 | Kleinert | | 73/628 |
| 2011/0247417 A1 * | 10/2011 | Oberdoerfer et al. | | 73/598 |

FOREIGN PATENT DOCUMENTS

| | | |
|---|---|---|
| DE | 102004027798 A1 | 1/2005 |
| DE | 102008037173 A1 | 7/2009 |
| DE | 102008002445 A1 | 10/2009 |
| DE | 102008002450 A1 | 10/2009 |
| WO | 2007/144271 A1 | 12/2007 |

OTHER PUBLICATIONS

International Search Report; PCT/EP2009/061579; Aug. 12, 2009.

* cited by examiner

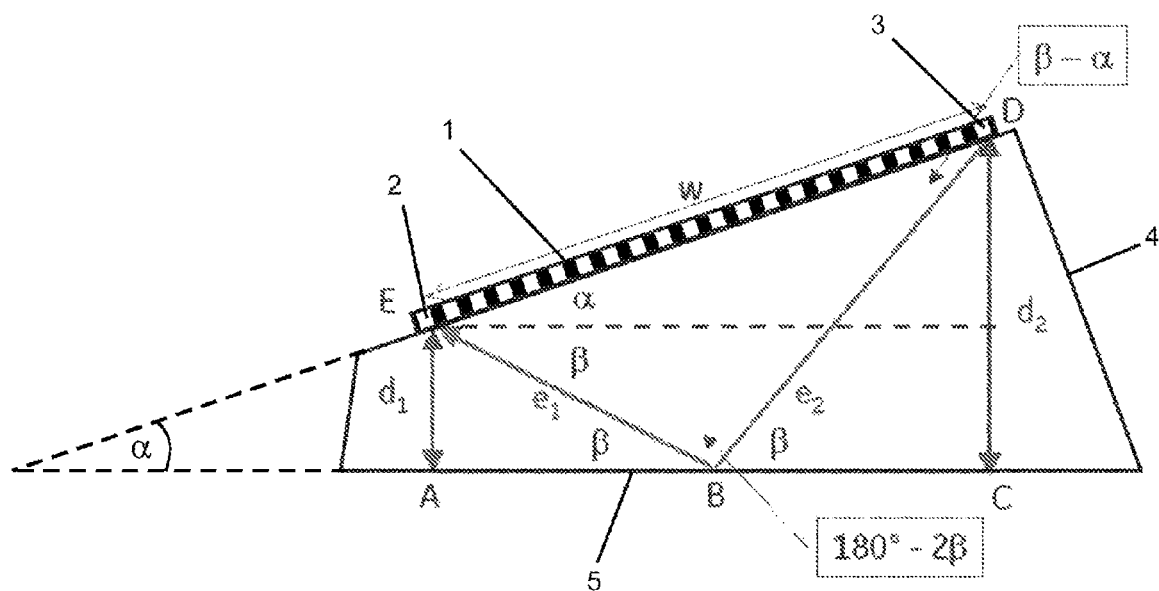

PULSE-ECHO METHOD FOR DETERMINING THE DAMPING BLOCK GEOMETRY

TECHNICAL FIELD

The invention relates to a pulse-echo method for ultrasound material inspection and a device therefor. This is an acoustic method for finding material flaws in which ultrasound is used. Ultrasound testing belongs to the non-destructive testing methods. In this manner, components can be inspected also in the fitted state, e.g. the supporting members of an airplane. Ultrasound testing is a suitable testing method for finding internal and external flaws in sound-conducting materials (to which most metals belong), for example in welding seams, steel forgings, cast, semi-finished products or pipes. In mechanical engineering, quality control of components is an important task in order to ensure, for example, the safety of passenger transport devices or of pipelines, for example for hazardous substances. Laid railroad tracks are routinely inspected by test trains. Therefore, the enhancement of the reliability and accuracy of these methods is intended.

BACKGROUND

Like all testing methods, ultrasound inspection is also standardized and is carried out in accordance with guidelines, such as according to DIN EN 10228-3 1998-07 Zerstörungsfreie Prüfung von Schmiedestücken aus Stahl—Teil 3: Ultraschallprüfung von Schmiedestücken aus ferritischem and martensitischem Stahl (Non-destructive testing of steel forgings—Part 3: Ultrasonic testing of ferritic or martensitic steel forgings), which is hereby incorporated by reference. Suitable testing devices and methods are known for the non-destructive testing of a workpiece by means of ultrasound. General reference is made to the textbook by J. and. H. Krautkrämer, Werkstoffprüfung mit Ultraschall, ISBN-13: 978-3-540-15754-0, 5th edition (1986), Springer (Berlin).

These methods are generally based on the reflection of sound on boundary surfaces. The sound source most frequently used is an ultrasonic probe or probe whose radiation is in the frequency range of 10 kHz to 100 MHz. In the case of the pulse-echo method, the ultrasonic probe does not emit a continuous radiation, but very short sound pulses with a duration of 1 μs and less. The pulse emanating from the transmitter passes through the workpiece to be inspected with the respective speed of sound, and is almost completely reflected at the solid-air boundary surface. The sound probe is most frequently not only able to transmit pulses, but also to convert incoming pulses into electrical measuring signals; it thus also works as a receiver. The time required by the sound pulse to travel from the transmitter through the workpiece and back again is measured with an oscilloscope or a computer unit as an evaluation unit. Given a known speed of sound c in the material, the thickness of a workpiece, for example, can thus be checked. The core of such a probe is at least one ultrasonic transducer, e.g. in the form of a piezo-electric element. Furthermore, it is known, for example from WO 2007/144271, to use a phased array of several, separately controllable ultrasonic transducers that are in a fixed spatial relation for the generation and reception of the ultrasonic pulses.

The transducer(s) are most frequently coupled to the workpiece to be inspected with a matching layer—also referred to as leading body—disposed therebetween and having, for example, a wedge shape and most frequently made of a thermoplastic synthetic material such as poly(methyl methacrylate) (PMMA). A coupling surface is provided on the leading body via which the sound generated by the ultrasonic transducer(s) can be coupled into the workpiece to be inspected, with the wedge shape causing the sound to enter into the workpiece obliquely. The leading body and the piezo-electric element (s) are generally disposed in a housing which is closed on its one side and which, on its other side, has a coupling aperture through which the ultrasound emitted by the sound coupling surface can exit.

In order to couple the workpiece and the probe, i.e. the leading body, a couplant (e.g. a glue (solution), gel, water or oil) is applied onto the surface of the workpiece to be inspected. The surface to be tested is most frequently passed over with the probe. This can take place manually, mechanically or automatically (for example in production lines). In the latter case, the test piece is often immersed in a suitable liquid (immersion technique) or wetted in a defined manner for the purpose of transmitting the sound signal.

The knowledge of the dimensions of the leading body that are relevant for the ultrasound inspection is, for example, essential for exactly locating flaws of a workpiece and/or for determining the dimensions of the workpiece. Furthermore, the geometry of the leading body has a strong influence on ultrasound inspections using the so-called DGS method, in particular if the latter is carried out with a probe that permits an electronic adjustment of the insonification angle. In the case of a wedge-shaped leading body, the dimensions relevant for the ultrasound inspection are, for example, the wedge angle alpha and the distance d between the coupling surface (i.e. the boundary surface contiguous to the workpiece to be inspected) of the leading body and the center of the surface covered by the transducers on the opposite boundary surface of the leading body.

It is known to configure the connection between the ultrasonic transducers and the leading body so as to be detachable, in order to be able to vary the inspection conditions, such as, for example, the insonification angle, during the ultrasound inspection of the workpiece, in accordance with the workpiece geometry to be inspected and/or the desired inspection direction. Moreover, it is known to store the specific data of the leading wedge in a non-volatile memory connected to the leading wedge and the read them out during the ultrasound inspection and transmit them to the evaluation unit. This is known, for example, from DE 3327526 A1, but proves to require a lot of effort in practice because data communication between the leading body and the evaluation unit is required. Moreover, faulty mounting of the leading body on the ultrasonic transducer (e.g. twisted direction of mounting) also cannot be detected in this manner.

Moreover, it was found that the dimensions of the leading body changes due to wear, which can be ascribed, among other things, to the frequently used thermoplastic, and thus often very soft, synthetic materials and the usually manual displacement of the leading body over a surface of the workpiece to be inspected. Consequently, a check of the dimensions of the leading body that are relevant for the ultrasound inspection is required. Basically, checking the dimensions of the leading body is known from DE 3327526 A1. However, this is done by means of a back-face echo of a special calibration body that must be disposed adjacent to the coupling surface of the leading body. This is comparatively complex and the measurement is adversely affected with regard to its accuracy by the variation of the calibration body and the coupling between the calibration body and the leading body.

Furthermore, the determination of the thickness in a workpiece using the back-face echo of the workpiece is known from DE 3441894 A1.

BRIEF SUMMARY

Against this background, the invention provides an improved, more accurate pulse-echo method in which the dimension(s) of the leading body relevant for ultrasound inspection are measured comparatively easily and, if necessary, taken into account in the evaluation of the ultrasound inspection.

In the method for the non-destructive ultrasound inspection, at least one ultrasonic pulse is radiated into a workpiece to be inspected by means of at least one ultrasonic transmitter. The invention is not limited with regard to the workpiece, but generally, it will comprise an acoustically conductive material. The ultrasonic pulse is reflected on boundary surfaces, for example its back face, and discontinuities in the workpiece. The reflected ultrasound is received by means of the at least one ultrasonic receiver and the associated signals are evaluated. The recorded signals are displayed, for example, in a time- or space-dependent representation, for example by an oscilloscope or a computer program product run on a computer with a display device. The space-dependent representation, for example, is linked to the time-dependent representation through the sound velocity. During its propagation from the transmitter to the workpiece and on the way back from the workpiece to the receiver, the ultrasound passes through a leading body disposed between the workpiece and the transmitter or receiver.

The method is characterized in that at least one step is provided that is precedent, intermediary or subsequent to the above-mentioned inspection, which serves for determining a dimension relevant for the ultrasound inspection, for example the thickness of the leading body and/or the angle of its boundary surfaces. In this step, the travel time of at least one ultrasonic pulse generated by the ultrasonic transmitter is reflected on a boundary surface of the leading body and received by the ultrasonic receiver. In other words, the travel time of the back-face echo of the leading wedge is determined, for example by means of the sound velocity and/or the distance between the transmitter and the receiver. At least one dimension of the leading body relevant for the ultrasound inspection is determined from the measured travel time. The terms receiver and transmitter are to be interpreted functionally. Therefore, it is provided in one embodiment according to the invention that a transducer acting as a transmitter also serves as a receiver of the ultrasonic pulse previously emitted by it. On the other hand, a different transducer spaced from the transmitter can serve as a receiver. The determination of the current dimension of the leading body, in a simple embodiment of the method according to the invention, can be used for checking it dimensional stability.

In addition, the geometrical data of the leading body that are relevant for the ultrasound inspection can thus be provided during the evaluation of the ultrasound inspection without any constructionally complex data exchange between the evaluation unit and the leading body or time-consuming manual data input. In addition, a wear-related deviation can be detected by the almost simultaneous measurement. No calibration body is required due to the measurement of the travel time of the back-face echo of the leading wedge. This simplifies the inspection and its accuracy and, if necessary, enables an in situ inspection. It should be clear to the person skilled in the art that he is able to enhance the accuracy of the determination by repeating the step for the determination of the dimension, by reversal of the sound propagation in the process and/or by using further transducers, i.e. sound paths.

According to another preferred embodiment, during the step for the determination of at least one dimension of the leading body, the latter is uncoupled. "Uncoupled" within the sense of the invention is to be understood to mean that the leading body is not acoustically coupled to the workpiece to be inspected. For example, it is coupled to air. The ultrasound propagation in the leading body is thus not affected by a coupled workpiece. In particular if a back-face echo is used, the reflectance and thus the accuracy of the determination is increased by a coupling to air, due to the large change of the acoustic impedance at the transition from the leading body to the ambient air. For this reason, an uncoupled state is to be understood, in principle, as the adjacency of the coupling surface to any medium, wherein the latter has a considerably different acoustic impedance from the material of the leading body, so that, preferably, an internal acoustical total reflection of the testing sound occurs in the leading body.

Preferably, the dimension is calculated by means of a sound path that corresponds to the respective travel time, is the shortest, obtained by geometric means or numerical simulation.

Furthermore, according to a preferred embodiment, the travel time of a back-face echo obliquely incident on the coupling surface adjoining, or to be adjoined to, the workpiece, and the travel time of at least one back face echo perpendicularly incident on the coupling surface are measured in the step for determining at least one dimension of the leading body relevant for the ultrasound inspection. It can be shown that, in the case of simple geometric configurations of the leading body, in particular in the case of a wedge shape, or in the case of two parallel boundary surfaces crossing the sound propagation, the calculation can by carried out by means of few travel time measurements, for example knowing only the distance of the ultrasonic transmitter and the ultrasonic receiver. Therefore, the method is preferably used in a leading body having a wedge shape or two plane-parallel surfaces. The shortest sound path of the ultrasound can thus be determined by simple geometric calculations from the travel time during the determination of the dimensions.

In a preferred embodiment, a phased array of selectively controllable ultrasonic transducers respectively acting as an ultrasonic receiver or transmitter is used for carrying out the method. Using a phased array opens up the possibility, by choosing the location and/or by the number of the selectively controlled transducers, of easily adapting the sound emission to the geometry and/or attenuation of the leading body in such a way that the emitted ultrasonic pulse actually reaches a receiver. Preferably, the phased array comprises more than two selectively controllable transducers.

In the step for determining at least one dimension of the leading body relevant for the ultrasound inspection, the outermost ultrasonic transducers of the phased array are preferably used in order to increase measurement accuracy.

Preferably, the determined dimension of the leading body is taken into account in the evaluation of the signals from the ultrasound inspection of the workpiece, in order thus to be able, for example, to determine with enhanced accuracy the position of a discontinuity relative to the position of the transmitting and/or receiving transducer(s).

The method is particularly suitable in the case of a leading body made from a thermoplastic synthetic material, in particular from a cross-linked polystyrene copolymer, for example Rexolite®, because they are subject to an increased wear and thus to a continuous and strong change of its dimensions.

In the evaluation in the step for determining the relevant dimension of the leading body, the signal of the receiving transducer of the phased array can be triggered to the rising flank or a zero crossing of the pulse echo in order to determine the travel time. Surprisingly, however, it was found that accuracy can be increased in the case of triggering to the pulse peak of the received pulse echo, which is why this process is preferably used. In this case, the evaluation can take place in a control unit (not shown) formed separately from the probe.

The digital and optionally analog electronic control system required for controlling the phased array in order to emit ultrasonic pulses can be combined therewith into a joint control and evaluating unit.

In another preferred embodiment of the method according to the invention, the dimension of the leading body determined within the context of the method according to the invention is taken into account in the evaluation of the test results. This may be relevant in particular if a phased array is used for generating the ultrasonic pulses for the material inspection, particularly, if, during the ultrasound inspection, it is controlled in such a way that the insonification angle into the workpiece is electronically adjusted in a controlled manner. By way of example, reference is made in this context to the patent applications DE 10 2008 037 173, DE 10 2008 002 445 and DE 10 2008 002 450 by the same applicants, which are connected to the generalizing expansion of the so called DGS method to testing devices with an electronically adjustable insonification angle. The aforementioned patent applications are hereby incorporated by reference into the content of the disclosure of the present application. However, a change of the dimensions of a wedge-shaped leading body can also be relevant with regard to a changed wedge angle alpha from which a change of the insonification angle into the material to be inspected also results immediately. If the thickness dimensions of the leading body are changed, this can result in a changed time of entry into the test object, which is relevant in the case of travel time measurements and determinations of positions correlated therewith. In a wedge-shaped leading body, this furthermore leads to a change of the coupling location. In preferred embodiments of the method according to the invention, all of the above-mentioned effects are also automatically compensated in the control of the phased array and/or taken into account when evaluating the test results. These particular process controls can be implemented, in particular, in the above-mentioned control and evaluation unit.

In one embodiment, the method furthermore comprises a step for determining a reference point of the leading body to be defined for the ultrasound inspection of the workpiece, for example an edge of the leading body, by the latter being disposed, for example, flush with the edge of a testing body and the back-face echo of this testing body being examined.

The invention moreover relates to a device for carrying out the method in at least one of the above-described advantageous embodiments. The device comprises at least one ultrasonic transmitter for emitting at least one ultrasonic pulse into a workpiece to be inspected, with the ultrasonic pulses being reflected on boundary surfaces in the workpiece. Moreover, at least one ultrasonic receiver for receiving the reflected ultrasound, an evaluation unit for evaluating the associated signals and a leading body are provided which is disposed between the workpiece and the transmitter such that the ultrasound passes through it. The device is characterized in that the ultrasonic receiver and the ultrasonic transmitter, for carrying out the step for determining the geometry of the leading body, are firmly or detachably connected thereto. In this step, the travel time of at least one ultrasonic pulse generated by the ultrasonic transmitter is reflected on a boundary surface of the leading body and received by said or a further ultrasonic receiver, measured, and at least one dimension of the leading body relevant for ultrasound inspection is determined therefrom. In other words, the travel time of at least one back-face echo of the leading wedge is determined. The terms receiver and transmitter are to be interpreted functionally. Therefore, it is provided in one embodiment according to the invention that a transducer acting as a transmitter also serves as a receiver of the ultrasonic pulse previously emitted by it. On the other hand, a different transducer disposed at a distance from the transmitter can serve as a receiver. By determining the current dimension of the leading body, its wear can be monitored and/or the accuracy of the ultrasound inspection carried out with the device can be increased. In addition, the geometrical data of the leading body that are relevant for the ultrasound inspection can thus be provided for the ultrasound inspection without any constructionally complex data exchange between the evaluation unit and the leading body or time-consuming manual data input. In addition, a wear-related deviation can be detected with certainty by the almost simultaneous measurement. No separate calibration body is required anymore because a measurement of the travel time of the back-face echo of the leading wedge is being carried out. This simplifies the inspection and its accuracy and, if necessary, enables an in situ inspection.

BRIEF DESCRIPTION OF THE DRAWING

The invention will be explained below with reference to a schematic illustration, such as the associated geometric calculations as well as a preferred embodiment, without limiting the invention to what is shown and described.

DETAILED DESCRIPTION

In the preferred embodiment of the method according to the invention, an ultrasound inspection by means of a pulse-echo method is carried out on a workpiece, which is not shown in FIG. 1, by means of the probe shown in FIG. 1. The phased array 1 of the probe which is also used in the determination of the dimension of the leading body 4, as will be described later, is used in this embodiment. The phased array 1 comprises several (in this case 22) selectively controllable sound transducers 2, 3. During the ultrasound inspection, they can be controlled jointly in phase, but jointly mutually out of phase, selectively in groups etc. The invention is not limited with regard to the process of the ultrasound inspection, and it is the responsibility of the person skilled in the art to select the respectively suitable controlling option. The ultrasound generated by the transducers of the phased array 1 passes through a leading body 4 of thermoplastic material in order to enter the workpiece, which is disposed adjacent to the coupling surface 5 of the wedge-shaped leading body 4 (hereinafter also referred to "leading wedge"). It should be noted that the sound velocity of the leading wedge 4 is comparatively strongly dependent on the temperature. As a rule, however, carrying out a separate temperature measurement on the leading body 4 is dispensable since the sound velocity c in the leading body is a direct result of the method according to the invention. In the event it is nevertheless advantageous under certain circumstances to know the absolute value T of the temperature of the leading body in addition to the sound velocity c, the temperature of the leading body can be deduced from tables for the material of the leading body based on the measured sound velocity c.

According to the invention, in order to increase the accuracy of the ultrasound inspection, a step for determining the dimension of the leading wedge 4 relevant for the ultrasound inspection is proposed. This step can be carried out before, after or in between the above-described ultrasound inspection and can be repeated several times, if necessary.

In this step, the phased array 1 is also used for ultrasound emission. Moreover, the leading wedge 4 is not coupled with its coupling surface 5 to a workpiece, i.e. it remains uncoupled, but, in particular, coupled to, for example, air. In this embodiment, the step comprises three individual steps. In two steps, the respective back-face echo of the strongly divergent sound beams generated, respectively, by the outermost transducers 2 and 3 is received by them, that is, the associated travel times $t_1$ and $t_2$ are determined, if the sound respectively hits the coupling surface 5 of the leading body 4 correctly, by means of the respective back-face echo. These steps can be offset in time, but also simultaneously. It should be noted that the shortest sound paths for the ultrasound are the paths $d_1$ and $d_2$, which correspond to the respective perpendicular distances of the transducers 2, 3 to the coupling surface 5. In a third sub-step, the travel time t of the ultra sound from the transducer 3 as a transmitter to the transducer 2 as a receiver (or vice versa) is measured while a back-face echo is formed, that is, in the case of an oblique incidence onto the coupling surface 5. The shortest sound path $e_1 + e_2$ of the ultrasound is characterized by the angle of incidence $\beta$ corresponding to the angle of reflection $\beta$ and the back-face (coupling surface 5).

In the case of a thicker, for example, wedge-shaped leading body, it may be advantageous if the above-described acquisition of the back-face echo on the uncoupled body is not carried out by means of the sound beam of a single transducer of the phased array, but if several (adjacent) transducers of the phased array are combined, for example, on the right edge and on the left edge in order to generate sound beams with a reduced divergence. Such a modified process control is also supposed to be comprised by the method according to the invention.

The sound velocity c in the leading wedge 4 can be determined from the three measured travel times t, $t_1$, $t_2$ and the known or previously determined (invariable) distance of the transducers w:

$$c = \frac{w}{\sqrt{t^2 - t_1 t_2}} = w(t^2 - t_1 t_2)^{-\frac{1}{2}} \quad (1)$$

The distances $d_1$ and $d_2$ can be calculated therefrom as follows:

$$d_1 = \frac{ct_1}{2} \quad d_2 = \frac{ct_2}{2} \quad (2)$$

The angle of elevation of the leading wedge can be determined from the equation $$\sin(\alpha) = \frac{d_2 - d_1}{w} \quad (3)$$

The mean distance d, which is not shown in the FIGURE, corresponds to the distance between the coupling surface and the center of the surface covered by the transducers 1 on the boundary surface of the leading body 5 opposite from the coupling surface 4 and is determined by:

$$d = \frac{d_1 + d_2}{2} \quad (4)$$

Regarding the derivation of the equation (1): $e_1$ and $e_2$ can be determined by means of the triangles $\triangle ABC$ and $\triangle BCD$:

$$e_1 = \frac{d_1}{\sin\beta} \quad e_2 = \frac{d_2}{\sin\beta} \quad (5)$$

The following applies for the sum of $e_1$ and $e_2$:

$$e_1 + e_2 = ct \quad (6)$$

Together with the above equations for $e_1$ and $e_2$, this corresponds to:

$$ct \sin \beta = d_1 + d_2 \quad (7)$$

Converting this, using the equations (2) for $d_1$ and $d_2$, the following is obtained:

$$\sin\beta = \frac{t_1 + t_2}{2t} \quad (8)$$

The following is obtained by means of the law of cosines of the triangle $\triangle BDE$:

$$w^2 = e_1^2 + e_2^2 - 2e_1 e_2 \cos(180° - 2\beta). \quad (9)$$

With $$\cos(180° - 2\beta) = 2\sin^2(\beta) - 1, \quad (10)$$

the use of the equations (4) and (9) yields:

$$w^2 \sin^2(\beta) = d_1^2 + d_2^2 - 2d_1 d_2 (2\sin^2(\beta) - 1)$$

The equations (2), (8) and (11) yield:

$$w^2 \left(\frac{t_1 + t_2}{2t}\right)^2 = c^2 \left\{ \frac{t_1^2}{4} + \frac{t_2^2}{4} - \frac{t_1 t_2}{2} \left( 2\left(\frac{t_1 + t_2}{2t}\right)^2 - 1 \right) \right\} \quad (12)$$

Or, correspondingly:

$$c = \frac{w}{\sqrt{t^2 - t_1 t_2}} = w(t^2 - t_1 t_2)^{-\frac{1}{2}}$$

In the illustrated wedge-shaped leading body 4 of the probe, the sound velocity c in the leading body 4 can therefore be determined, in the case of oblique incidence of the back-face echo, by measuring the travel times t, $t_1$, $t_2$, and because of the distance w from the transmitter 3 and the receiver 2. The sound velocity c, which has thus been accurately determined and exists in actual fact, serves for calculating the perpendicular distance $d_1$ and $d_2$ of the receiver 2 or the transmitter 3 to the coupling surface 5. The evaluation of the actual ultrasound inspection is then based upon them, thus increasing its determination accuracy.

The invention claimed is:

1. A method for non-destructive ultrasound inspection, wherein at least one ultrasonic pulse is radiated into a workpiece to be inspected by means of at least one ultrasonic transmitter and the ultrasonic pulse is reflected on boundary surfaces in the workpiece, the reflected ultrasound is received by means of the at least one ultrasonic receiver and at least one associated signals are evaluated, and the ultrasound passes through a leading body which is disposed between the workpiece and the transmitter or receiver and is detachably connected to the ultrasonic transmitter and the ultrasonic receiver, wherein the method comprises at least one step for determining at least one dimension of the leading body, in which the travel time of the at least one ultrasonic pulse generated by the ultrasonic transmitter is reflected on a boundary surface of the leading body and received by the ultrasonic receiver, measured, and at least one dimension of the leading body relevant for ultrasound inspection is determined therefrom, wherein, in the step for the determination of at least one dimension of the leading body relevant for the ultrasound inspection, the leading body is uncoupled, wherein, in the step for the determination of at least one dimension of the leading body relevant for the ultrasound inspection, the travel time of a back-face echo obliquely incident on a coupling surface adjoining, or to be adjoined to, the workpiece, and the travel time of at least one back-face echo perpendicularly incident on the coupling surface are measured, wherein a phased array of selectively controllable ultrasonic transducers respectively acting as an ultrasonic receiver or transmitter is used, wherein, in the step for the determination of at least one dimension of the leading body relevant for the ultrasound inspection, the determination is carried out by means of triggering to a pulse peak of the received pulse echo, wherein the determined dimension of the leading body is taken into account in the evaluation of the signals in the ultrasound inspection of the workpiece.

2. The method according to the claim 1, wherein the dimension is calculated by means of a sound path that corresponds to the respective travel time, is the shortest, is obtained by geometric means or numerical simulation.

3. The method according to claim 1, wherein the sound velocity c in the leading body is determined when the method is carried out.

4. The method according to claim 1, wherein the phased array comprises more than two selectively controllable ultrasonic transducers.

5. The method according to claim 1, wherein, in the step for determining at least one dimension of the leading body relevant for the ultrasound inspection, the outermost ultrasonic transducers of the phased array are used.

6. The method according to claim 1, wherein the leading body used has a wedge shape or two plane-parallel surfaces.

7. The method according claim 1, wherein the leading body used consists of a thermoplastic synthetic material, in particular a cross-linked polystyrene copolymer.

* * * * *